United States Patent
Sabet

(10) Patent No.: US 9,383,345 B2
(45) Date of Patent: Jul. 5, 2016

(54) METHOD FOR CULLET QUALITY GRADING

(71) Applicant: Saint-Gobain Containers, Inc., Muncie, IN (US)

(72) Inventor: Shahriar Sabet, Yorktown, IN (US)

(73) Assignee: Ardaugh Glass Inc., Muncie, IN (US)

( * ) Notice: Subject to any disclaimer, the term of this patent is extended or adjusted under 35 U.S.C. 154(b) by 312 days.

(21) Appl. No.: 13/930,294

(22) Filed: Jun. 28, 2013

(65) Prior Publication Data

US 2013/0283937 A1    Oct. 31, 2013

Related U.S. Application Data

(62) Division of application No. 12/831,177, filed on Jul. 6, 2010, now Pat. No. 8,528,428.

(60) Provisional application No. 61/223,311, filed on Jul. 6, 2009.

(51) Int. Cl.
| G01N 33/38 | (2006.01) |
| G01N 33/15 | (2006.01) |
| G01N 1/04 | (2006.01) |
| G01N 5/04 | (2006.01) |

(52) U.S. Cl.
CPC .............. *G01N 33/15* (2013.01); *G01N 33/386* (2013.01); *G01N 1/04* (2013.01); *G01N 5/04* (2013.01)

(58) Field of Classification Search
CPC .................................................. G01N 33/386
USPC .......................................................... 73/866
See application file for complete search history.

(56) References Cited

U.S. PATENT DOCUMENTS

| 3,837,831 A | 9/1974 | Moore |
| 4,252,551 A | 2/1981 | Nishimura |
| 4,347,073 A | 8/1982 | Aubourg et al. |
| 4,422,862 A | 12/1983 | Wardlaw |
| 4,457,772 A | 7/1984 | Haynes et al. |
| 5,352,258 A | 10/1994 | DeGreve et al. |

(Continued)

FOREIGN PATENT DOCUMENTS

| EP | 0709138 | 1/2000 |
| EP | 1666427 | 6/2006 |
| WO | 2007044956 | 4/2007 |

OTHER PUBLICATIONS

Nix, M., et al., Calculation of the redox number of glass batches containing recycled cullet, International Journal of Glass Science and Technology, International Conference "Advances in the Fusion and Processing of Glass," Oct. 22-25, 1990, pp. 271-279, Dusseldorf.

(Continued)

*Primary Examiner* — Hezron E Williams
*Assistant Examiner* — Nashmiya Fayyaz
(74) *Attorney, Agent, or Firm* — John V. Daniluck; Brian W. Chellgren; Bingham Greenebaum Doll LLP

(57) ABSTRACT

A method for grading the quality of cullet. Some embodiments include methods for generating a statistically significant sample of material from a collection of cullet contaminated with waste. Other embodiments include methods for evaluating various qualities of the sample with relatively simple techniques. Yet other embodiments include a uniform and reasonably simple method for communicating the results of the evaluation among different parties.

6 Claims, 7 Drawing Sheets

(56) References Cited

U.S. PATENT DOCUMENTS

| | | |
|---|---|---|
| 5,399,181 A | 3/1995 | Sorg |
| 5,663,997 A | 9/1997 | Willis et al. |
| 5,741,342 A | 4/1998 | Alexander |
| 5,779,748 A | 7/1998 | Alexander |
| 5,855,636 A | 1/1999 | Alexander |
| 5,894,938 A | 4/1999 | Ichise et al. |
| 5,954,851 A | 9/1999 | Sakae |
| 6,230,521 B1 | 5/2001 | Lehman |
| 6,810,301 B2 | 10/2004 | Lehman |
| 7,350,379 B2 | 4/2008 | Ueda et al. |
| 7,351,929 B2 | 4/2008 | Afsari et al. |
| 7,383,695 B2 * | 6/2008 | Lehman et al. ............... 65/29.16 |
| 7,386,997 B2 | 6/2008 | Lehman et al. |
| 7,565,816 B2 | 7/2009 | Lehman et al. |
| 2003/0032370 A1 | 2/2003 | Balcar et al. |
| 2006/0000237 A1 | 1/2006 | Bohlig et al. |
| 2006/0101856 A1 | 5/2006 | Lehman et al. |
| 2006/0230787 A1 * | 10/2006 | Lehman et al. ............... 65/27 |
| 2007/0012599 A1 | 1/2007 | Bohlig et al. |
| 2008/0156039 A1 | 7/2008 | Lehman et al. |
| 2008/0237093 A1 | 10/2008 | Bohlig et al. |

OTHER PUBLICATIONS

Faber, A.J., et al., Technological impacts of glass recycling, Chinese Ceramic Society, Proceedings of XVII International Congress on Glass, Glass Technology, Glass Archeometry, 1995, pp. 151-156, vol. 6, Beijing.

Shimono, Fujio, et al., A Calculation Method to Predict the Colour of Glass, Glass, Feb. 1983, pp. 61-63, vol. 60, No. 2, Sussex.

Usvitskii, M.B., Calculation of the Batch Composition with a Microcalculator, State Scientific-Research Institute of Glass, Translated from Steklo i Keramika, Apr. 1983, pp. 7-9, No. 4.

Anderson, D.W., Minimizing Glass Batch Costs Through Linear Programming, Ceramic Engineering & Science Proceedings, Mar.-Apr. 1994, pp. 19-24, 15[2], Westerville, Ohio.

Methods for Sampling and Testing Recycled Glass, Clean Washington Center, Dec. 1996.

* cited by examiner

METHOD FOR CULLET QUALITY GRADING

CROSS REFERENCE TO RELATED APPLICATION

This divisional application claims the benefit of priority to U.S. patent application Ser. No. 12/831,177, filed Jul. 6, 2010, entitled METHOD FOR CULLET QUALITY GRADING, incorporated herein by reference, which claims the benefit of U.S. Provisional Patent Application Ser. No. 61/223,311, filed Jul. 6, 2009, entitled METHOD FOR CULLET QUALITY GRADING, incorporated herein by reference.

FIELD OF THE INVENTION

Various embodiments of the present invention pertain to methods for determining the quality of cullet, and in particular to methods for analyzing the color and sizing of the cullet, organic material on the cullet, or inclusion of non-glass materials.

BACKGROUND OF THE INVENTION

The multifunctional role of cullet as an endless cradle to cradle sustainable material has resulted in its increased use within the glass industry. This is even more pronounced in light of recent spiraling energy prices. However, availability of high quality post consumer cullet is a challenge due to contamination during the recycling process. So far to the author's knowledge, there are no systematic methods to determine the type of contamination and also to express the severity of said contamination in a truck load or a pile of cullet. This work in one embodiment establishes a practical quality index to specify cullet quality by type and severity of contaminants. This coding method can be used by all parties involved in the life cycle of cullet (i.e. cullet suppliers and glass manufacturing industries).

Cullet can be used in the glass manufacturing process in any percentage up to ~90% depending on availability, quality and price. The advantages of addition of cullet to raw batch can be summarized as:
1. Cullet accelerates the melting process by wetting the batch materials and hence aiding decompositions and/or reactions to take place faster.
2. Based on empirical data, every 10% of cullet can result a saving of ~3-4% in energy consumption.
3. Use of cullet improves sustainability by reducing the quarrying of virgin raw materials; every 100 tons of cullet results in a reduction of 120 tons of virgin materials, assuming normal fusion loss factors.
4. As a result of the aforementioned benefits of reducing energy and reduction of raw materials, cullet results in reduced emitted gases like $CO_2$, $SO_x$ and $NO_x$.

Various embodiments of the present invention establish a practical quality index to specify quality of cullet as far as type and severity of contaminants. Some embodiments of the inventive method of coding described herein can be used by all parties in the life cycle of cullet i.e. cullet suppliers and glass manufacturing industries.

DESCRIPTION OF THE PREFERRED EMBODIMENT

Figure 1:
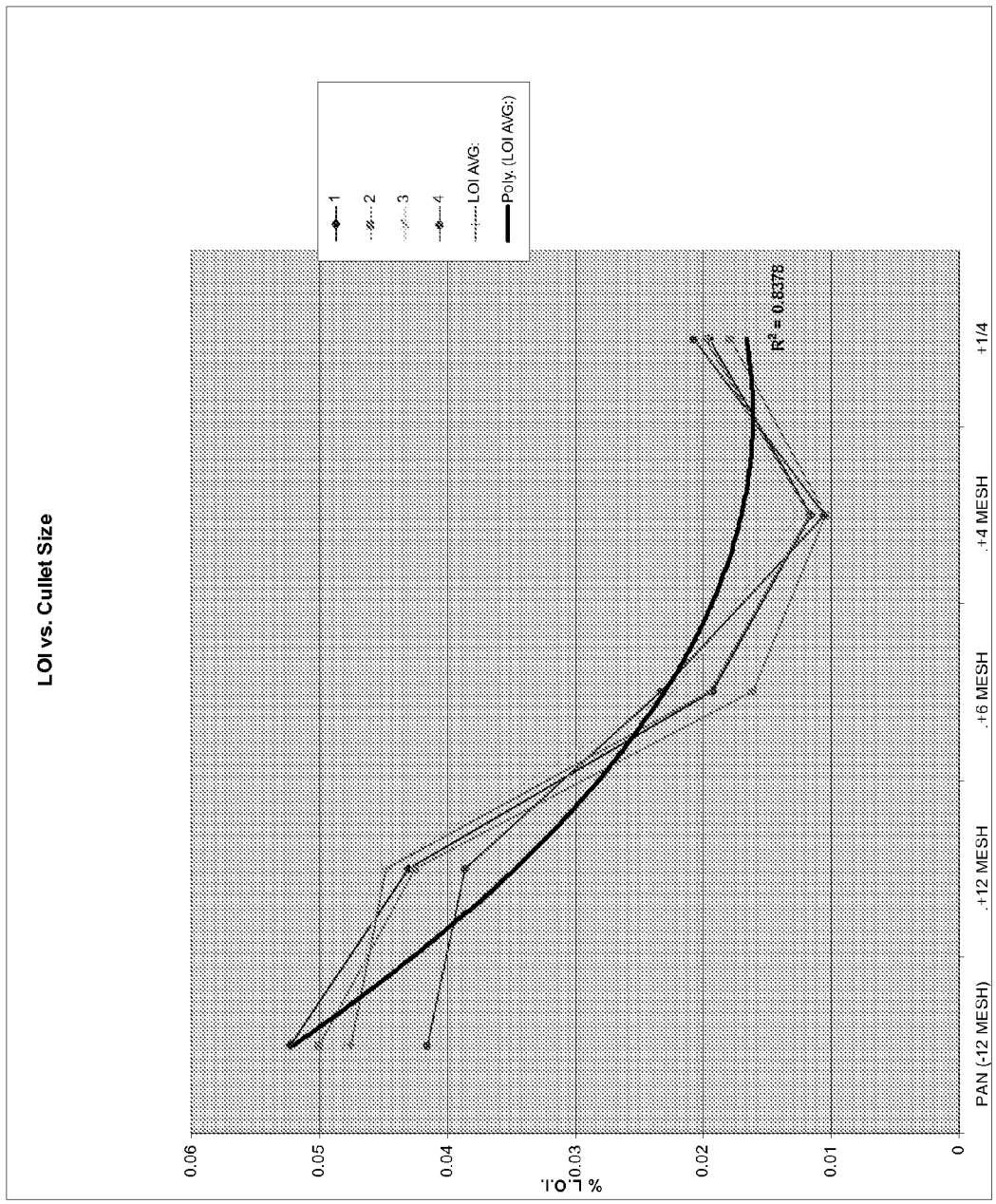
FIG. 1 is a graphical representation particle size vs. LOI percentage showing the results of tests done on 6 samples showing that LOI increases within the smaller pieces of cullet.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

The U.S. and Europe have different methods for collecting and using cullet. In Europe, it is common for cullet to be entirely separate from other waste streams, such as paper, metals, and organics (such as food waste). In some cases, cullet is even separated by color. In such a waste collection system, there is relatively little contamination of the cullet with any of the other waste streams. Further, if a glass manufacturer needs to know how to present the proper mix of ingredients to the glass furnace, it is relatively straight forward to mix the cullet with various correcting agents.

In contrast, recycled material in the U.S. is largely a co-mingled, single stream of waste from the house or curbside to the waste processors. These processors must separate as best they can those waste products that have economic value, such as cullet and aluminum. Even after such gross processing of the single stream of waste products, the separated waste streams can still contain significant amounts of co-mingled waste. For example, the separated cullet may have come from food containers, in which case there is food residue on the cullet. Further, some objects such as porcelain, ceramics, and stones are often still co-mingled with the cullet. The cullet may further contain various pieces of metal that were not of a size, composition, or character to have been successfully separated out.

Therefore, in the U.S. the cullet provided by waste processors to glass manufacturers typically contains unknown, significant, and variable amounts of contaminant. In order to maintain the economic viability of recycling the cullet, the cullet should not have too many contaminants that will damage the glass manufacturers facilities, or result in undesirable glass containers. If the degree of contamination is not known, then damage to the manufacturing equipment or fabrication of unsafe containers can lead to economic consequences that overwhelm the energy savings and beneficial environmental effects by the use of cullet.

In addition, if it is too expensive to assess, grade, and categorize the contaminated cullet, then the price of the cullet can be high enough to offset the beneficial environmental aspects of the cullet usage. As one example, if the waste processor is required to have expensive treatment, sampling, and chemical analysis facilities, then he will commensurately increase the price of his cullet, which results in reduced usage.

A further complication of contaminated cullet prepared by waste processors and sold to glass manufacturers arises from the non-homogeneous nature of the contaminated cullet. Often, the cullet is not mixed, and one local area of a pile of contaminated cullet may have excessive types of particular contamination (such as green glass) that is not representative of the entire pile. Therefore, if samples are taken from the pile for further analysis, the samples will be skewed if care is not taken to be statistically significant in the sampling method.

Yet another complication in the U.S. of contaminated cullet is the lack of a common grading and categorization method between cullet providers and cullet users. One embodiment of the present invention pertains to a grading method for assigning a multidigit number as representative of the quality of the cullet within a specific quantity (or pile) of contaminated cullet. In one embodiment, the grading method includes four digits, with one digit representative for various grades of each of the color; organic and moisture content; porcelain, ceramics, stones (PCS) and metals and different glasses; and the size of the particles of cullet. One embodiment pertains to assessing each of these four qualities of the cullet pile with numbered grades (such as a grade of 1 being best and a grade of 6 being worst). It is appreciated that the different quality categories could be represented by letters or symbols, and further that the order of the four qualities within the multidigit number is arbitrary. Further, in some situations where a supplier is known to be consistent with regards to one or more qualities, that cullet supplier may be asked to only provide grades in the inconsistent qualities.

One embodiment of the present invention pertains to a method for consistently grading a quantity of cullet without the need to resort to testing requiring specialized laboratory facilities. In one embodiment, the organic content of the cullet is established by drying a representative sample of the cullet, weighing the sample, rinsing the sample with a fluid such as water, and re-weighing the sample. The method results in the determination of a weight loss on rinsing (LOR) that is useful in predicting the organic content of the entire sample.

Yet another embodiment of the present invention pertains to a method for establishing a statistical basis for analyzing the presence of various contaminants in a load of cullet. The method includes creating a first number of pilot samples taken from different locations of the load. The method includes making a first assessment of a contaminant from the first pilot samples. In some embodiments, the first assessment is for the number of pieces of porcelain, ceramics, stones, and metals. In some embodiments, the first number of pilot samples is reduced to a statistically significant yet reduced second number of piles. From this smaller second number of samples, additional assessments can be made of the cullet, such as the color content, size content, or organic content.

Yet other embodiments of the present invention pertain to a method for establishing statistically significant samples from a load of cullet, such as a load of cullet and other waste material and recyclable material dumped from a truck and into a pile. In one embodiment, the method includes taking a number of pilot samples from a predetermined height of the pile. In one embodiment, the predetermined height is about half-way from the base of the pile to the top of the pile. The method further includes taking a number of pilot samples around the circumference of the pile. In some embodiments, the samples are taken from the pile at approximately equally spaced locations around the circumference of the pile. In still further embodiments an equal number of samples are taken.

The method further includes eliminating at least a pair of samples that are spaced apart and on opposite sides of the pile. The remaining samples are then remixed into a second central pile. A second predetermined number of pilot samples are taken from the second pile. Preferably, the second number of samples are taken at locations around the second pile that are circumferentially equidistant from one another, and further preferably from a location intermediate of the base and the top of the second pile. From this second arrangement of pilot samples, a pair of samples from opposite sides (i.e., about 180 degrees opposite each other) are removed.

This aforementioned process of taking equally spaced samples, eliminating oppositely placed samples, and remixing the remaining samples can continue until the remaining sample size is suitable for further analysis of color, size, or organic content. Preferably, in the final step of the process there are only two samples remaining that are in opposite quadrants of the final central pile. In yet other embodiments the final mixture of samples is spread evenly over an area and divided into equal sectors (or in some embodiments, for equal quadrants). Preferably, two opposite sectors (or two opposite quadrants) of the final mixed sample are retained. One sector is used for further measurements, and another sector is kept for reference purposes.

One embodiment of the present invention pertains to a method for assessing the water content of a batch of cullet glass. In one embodiment, the method includes determining the weight loss of a measurement sample that occurs as a result of drying. In one embodiment, the measurement sample is first weighed in its contaminated state. The measurement sample is then dried in air at a temperature preferably chosen to evaporate water (such as about 110 degrees C.), but not so high a temperature as to oxidize any organic contaminants. After drying, the measurement sample is weighed again. This loss in weight can be expressed as a percentage of the total weight of the sample. In some embodiment this percentage loss is referred to as the loss on rinsing (LOR), and can be used to adjust the total weight of the pile of cullet, especially in those applications where the cullet is purchased on a weight basis.

Yet another embodiment of the present invention pertains to a method for assessing the organic content of a batch of cullet glass. In one embodiment the method includes rinsing a measurement sample of the batch with water. In some embodiments the temperature of the water is slightly elevated to about 80 degrees C. The rinsing continues until the water draining from the measurement sample is clear, indicating that organic contaminants have been washed away. The sample is dried, and the weight of the rinsed and dried cullet is compared to the weight of the dry cullet prior to rinsing. The measurement sample's weight loss on rinsing (LOR) can be used to categorize the pile (or initial batch) of cullet with regards to its contamination by organic materials (such as food, paper, etc.).

Further, it has been found that LOR correlates generally to the weight loss on ignition (LOI) of the sample. In those cases where LOI is used to assess cullet, the LOR can be substituted and used in the assessment.

Yet another embodiment of the present invention pertains to methods for assessing the characteristics of a collection of cullet that can be done simply and without expensive equipment, yet still protecting the glass furnace. One embodiment includes a method for acquiring a representative sample of raw cullet (i.e., contaminated) from a larger collection of cullet. In one embodiment, the method includes providing a quantity of raw cullet, such as a truckload of cullet from a waste material processor. The truckload is dumped onto a surface in a pile. Samples are taken from a point midway between the top of the pile and the bottom of the pile, so as to minimize biasing of contaminants in the sample due to settling of the raw cullet. Further, samples are taken from circumferential points generally equidistant around the mid-height of the pile. These pilot samples are then arranged relative to each other in a manner generally corresponding to the circumferential location of the pile from which they were taken. In this way, if a particular location within the pile is biased (such as to include large amounts of a particular color of glass), the final effect of the biasing on the homogeneity of the measurement sample will be minimized.

The more common ways of categorizing contaminant materials in cullet are usually based on the type of contaminants. This paper presents various methods of detection of contaminants resulting in a simple way of coding to specify the quality of large volume piles of cullet.

It is common practice in the glass industry to use mixed cullet in the production of colored glasses such as amber and greens. But variation of the proportions of different colors can result in problems. For example, in a 3 mix cullet the proportions of green, amber and flint should be consistent to assure the consistency of quality as well as the color of the finished glass products. Flint cullet is used to help control the redox of colored glasses. Therefore, uncontrolled variations of flint cullet will result in fluctuations in the redox from the targeted value in the batch formulation. In flint glass manufacture, the existence of colored cullet would also affect the color parameter mainly as a result of presence of Chromium, Iron Oxides, Sulfur, and Carbon from colored cullet.

Visible organics, paper, wood, cork, plastics, rubbers and even fabrics, are not uncommon in many cullet sources. Invisible organics such as fat, oil, sugar and other carbohydrates in post consumer cullet are inevitable contaminants. Unknown and uncontrolled amounts of organics in cullet will directly affect the redox condition of the glass, resulting in refining issues as well as color variations. Based on empirical experiments, the following relations can be assumed for different organics:

$$1 \text{ unit wt. of carbon} = 20 \text{ units paper} = 4 \text{ units plastic} = 0.8 \text{-} 0.9 \text{ units fat or oil} = 1 \text{ unit sugar}$$

Common practice for reducing organics in cullet is to stock the cullet for at least 4-6 weeks. This, together with enough moisture, allows disintegration of much of the organic material within the pile. By allowing time for disintegration, the level of organics tend to a constant value and in this way the glass technologist can make more accurate adjustments with regards to the amount of carbon in the batch to ensure the required redox is achieved.

PCS contaminants (porcelain, ceramics, and stones) are the major cause of stones in finished glass products. The majority of stones found in finished products derive from PCS contamination in the cullet stream.

Metals, both ferrous and non-ferrous (lead, aluminum), have different effects on the quality of finished product as well as on the life of furnace refractories. For instance, large pieces of iron result in downward drilling on the bottom paving refractories, resulting in glass running between the insulation layers, and eventually causing bottom failures. Lead, usually from wine bottle seals, and light bulb components, increases the amount of heavy metals content in finished glass product. Metallic aluminum causes so called "silicon balls" by reducing $SiO_2$ to elemental Si.

The presence of cullet with different fundamental chemistry in the host glass is a major cause of knots. In the case of production of soda-lime glass, other glasses such as aluminosilicate, borosilicate, lead crystals and vitreous silica within the feed cullet can create knots and/or cords due to their higher melting temperatures and higher viscosities at normal melting temperatures of soda-lime glasses.

Another consideration in the use of cullet within the glass industry is with regards to the size of the cullet pieces. In some instances, it is preferred to use fine ground cullet with the logic that stones and ceramic contaminations will be ground to smaller pieces and hence the risk of finding their way to the finished product is reduced. In yet other situations, it is considered that ground cullet carries a considerable amount of "invisible" organics that affect redox.

In one embodiment of the present invention, it is contemplated that the size of the cullet pieces are between about ¼" and about 2" in dimension. Pieces larger than about 2" often result in blocking within conveying chutes while pieces smaller than about ¼ " are considered susceptible to carry a large proportion of "invisible organics" due to the high surface area to volume ratio. FIG. 1 shows organic contents in smaller pieces of cullet start picking up among the sizes smaller than ¼".

Based on the previously mentioned categories of cullet contaminants, one embodiment of the present invention contemplates a system of coding indicates the type and the severity of each contaminant. This coding takes the form of a multidigit number, such as a 4 digit number, which can be referred to in some embodiments as the COPS Code. Each digit represents one of the following parameters:

C: for Color
O: for Organics
P: for PCS (Porcelains, Ceramics and Stones), metals and other types of glasses, and
S: for Size of the cullet pieces Where each letter would be replaced with an integer from 1 to 6 in which 1 would indicate the best grade and 6 would be the worst grade.

In one embodiment of the present invention, a representative sample is taken for the measurements, such as from a truck load of cullet, unloaded on the ground. The unloaded pile is preferably divided into 8 zones as shown, looking from the top, as shown in FIG. 3.

Figure 4:
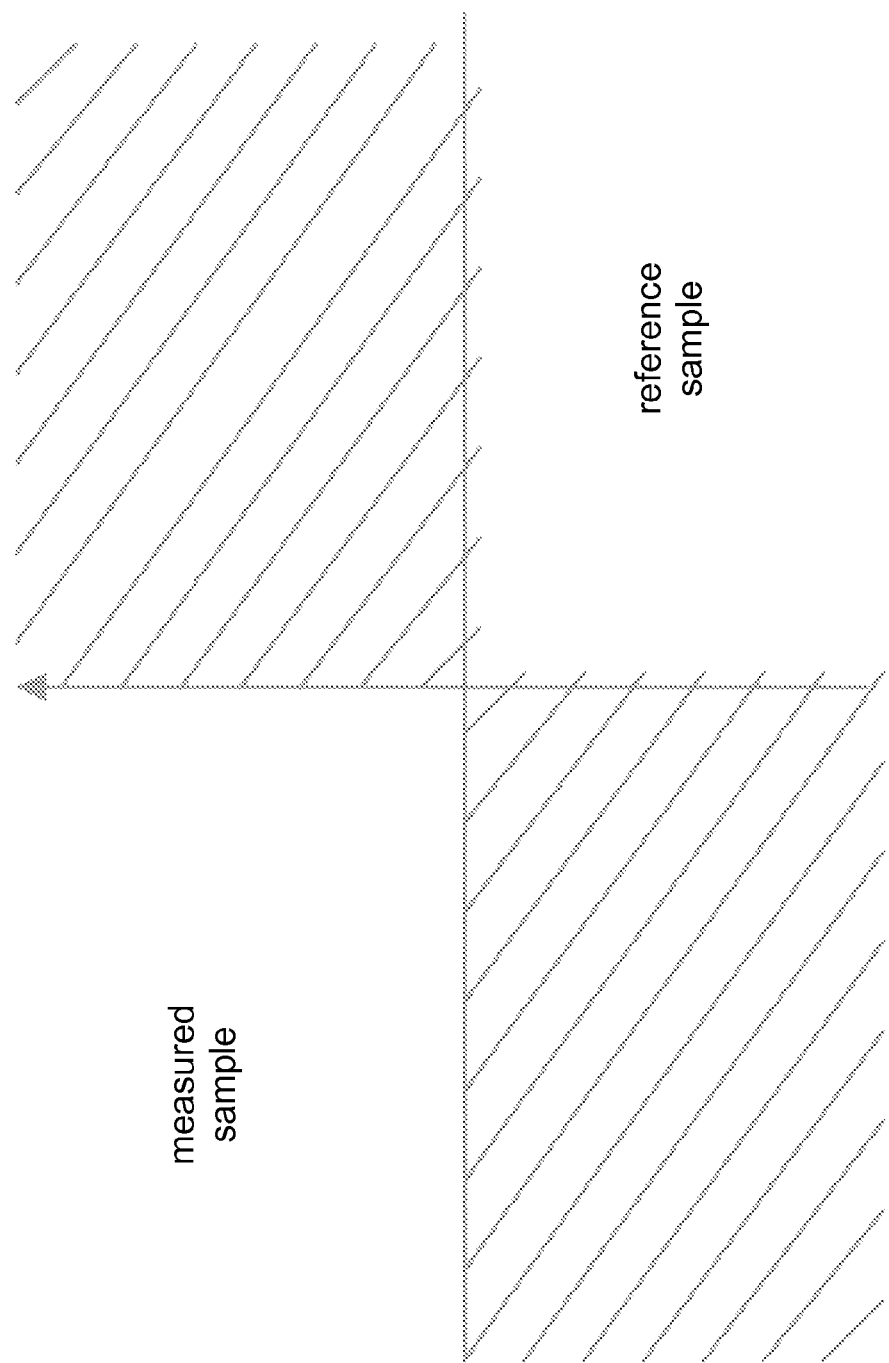
FIG. 4 is a schematic representation looking down on a mixture of split samples separated into four sectors.

Using a scoop with the approximate capacity of 6 pounds take 1 sample form each spot from the mid height of the pile by dipping the scoop inside the pile. Therefore, the total sample will be around 48-50 pounds. Spread the sample on a clean area next to the cullet pile and look for the PCS, metals and other types of glasses which are larger than 1/4". Mix the sample in place by using the scoop and make a cone. Divide it into 4 sections as shown in FIG. 4. Discard the 2 opposite quadrant and choose the other. Now 24 pounds of sample is left. Repeat steps 4-6 till around 3 pounds of sample is left on the ground. Now take this sample to the lab (any room used for the rest of measurements). For the last time split the 3 pound sample into 4 sections. Each section now is around 3/4 of a pound or 12 oz. or 340 gr. which is called small split sample throughout this paper. Save and label one part for future references and use each of the other parts for different measurements.

The following is the sequence of the measurements for each category according to one embodiment. With regards to PCS, metals and different glasses, foreign materials in the cullet are divided into 2 different parts with respect to the size of pieces. One part pertains to pieces greater than 1/4" which usually have the potential to appear as an inclusion defect in the final glass product, and the other part refers to pieces smaller than 1/4" which usually will get melted in the furnace and subsequently pose less of a risk for inclusions in the finished glass product.

Figure 3:
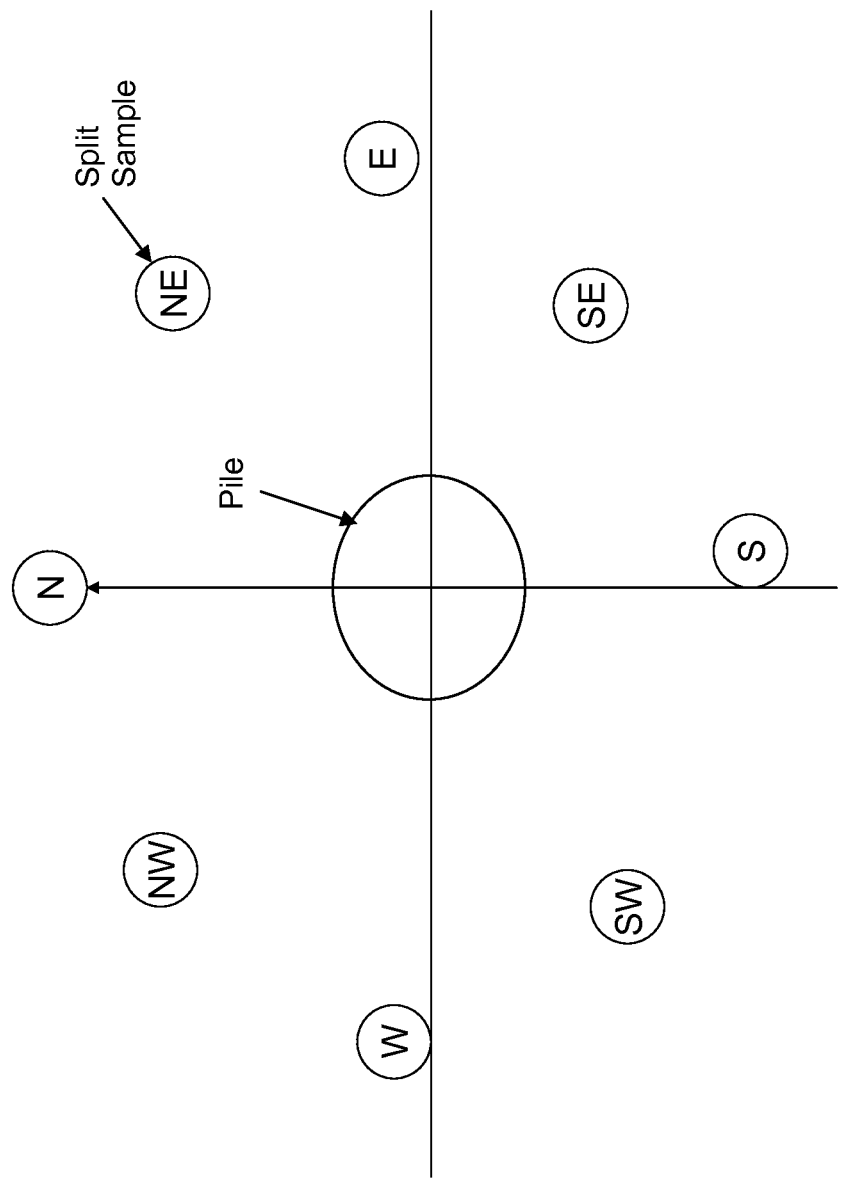
FIG. 3 is a schematic representation looking downward on a pile of contaminated cullet surrounded by a plurality of split samples.

For sizes greater than 1/4" use the entire 48 lb. representative sample (as shown in FIG. 3) before splitting into split samples. Then count the number of big sizes that are almost equal or greater than 1/4 inch in one dimension. The material can be categorized according to, in one embodiment, Table 3 for criteria of grading.

For particles smaller than 1/4" (if any) one of the small measured samples (as shown in FIG. 4) will be used for measuring the weight percentage of the fine particles over the total wt of the sample. See Table 3 for categorizing of each grade.

With regards to size of the cullet pieces, using one of the small split samples (as shown in FIG. 4), the technician is to then weigh the sample (W total). The technician then segregates the pieces which are smaller than 1/4" and bigger than 2" and weigh (W off size). Following segregation, the technician calculates the weight percentage of off size cullet pieces with respect to the total weight.

With regards to color, in a flint cullet, any color other than flint would be off color, or in a 2 mix cullet like green and amber if your agreement with the supplier is to receive a proportion of 40/60 then any deviation from the expected proportions will be considered as off color.

To measure the percentage of off color the technician uses the segregated part (pieces between 1/4 and 2") from the above sample used for size of the cullet pieces. The technician weighs the sample. The technician then segregates the different colors and weighs each part. Following segregation, the technician calculates the weight percentage of each part versus the total weight of the sample. Table 1 shows the criteria for the color variations for each grade.

With regards to organics and moisture, there are three recognized methods for the determination of the amount of organics in cullet: Loss on Ignition (LOI), Chemical Oxygen Demand (COD) and Partial pressure of Oxygen in a cullet melt. LOR (Loss on Rinsing) is a method according to one embodiment of the present invention that avoids some of the complications of the aforementioned other methods. Some of the other methods, such as LOI, can require the use of equipment that the cullet supplier may not have. In contrast, the LOR method in some embodiments uses methods and equipment that do not require special training or skills.

To measure LOR take one of the measured samples of the total sample (the pile) and perform the following acts on the measured sample:

I. Weigh the sample ($W_1$).

II. Dry the sample at 110° C. for 15-20 minutes and cool it down.

III. Weigh the sample again ($W_2$).

IV. LOD %=$(W_1-W_2)/W_1 \times 100$

V. Place the sample in a 100 mesh screen (or a flat dish) and rinse the sample with hot water (80° C.) till the water runs clear—if using the flat dish make sure not to lose the fine particles of cullet counting them as the organics.

VI. Dry the sample again at 110° C. for 15-20 minutes and cool it down.

VII. Weigh the sample ($W_3$).

VIII. LOR %=$((W_2-W_3)/W_2 \times 100$.

The following four tables present various categories for assessing the aforementioned tests on the samples of cullet. Table 1 refers to the grading criteria and categories for evaluating how much the pile of cullet deviates from the desired color characteristics. For example, it may be desired that the cullet be 100 percent flint. In such a case a grade of 1 would be established for samples having three percent of their cullet (by weight) being of a non-flint color. As yet another example, it may be desirable to obtain cullet that is a combination of green and amber (for example, a 60 percent/40 percent split of green and amber, respectively). In this case, green and amber measurements of 56.5 percent and 43.5 percent, respectively, would result in the material being categorized with a grade above 2.

Table 2 presents the criteria for grading of organics and moisture in a pile of cullet. In one embodiment, each of the six grades can be based either on the LOD measurement or the LOR measurement. Further, in Table 2 as well as the other tables, it is to be appreciated that the various criteria for grading are by way of example only, and are not intended to be limitations to any of the inventions disclosed or claimed herein.

TABLE 1

| Grading criteria and categories for off color. | |
|---|---|
| Grade | Criteria |
| 1 | off color ≤ 3% |
| 2 | 3% < off color ≤ 4% |
| 3 | 4% < off color ≤ 5% |
| 4 | 5% < off color ≤ 6% |
| 5 | 6% < off color ≤ 7% |
| 6 | off color > 7% |

TABLE 2

Grading criteria and categories for organics and moisture.

| Grade* | Criteria |
|---|---|
| 1 | 0.5% < LOD ≤ 1.0% AND/OR LOR ≤ 1.0% |
| 2 | 1.0% < LOD ≤ 1.5% AND/OR 1.0% < LOR ≤ 1.5% |
| 3 | 1.5% < LOD ≤ 2.0% AND/OR 1.5% < LOR ≤ 2.0% |
| 4 | 2.0% < LOD ≤ 2.5% AND/OR 2.0% < LOR ≤ 2.5% |
| 5 | 2.5% < LOD ≤ 3.0% AND/OR 2.5% < LOR ≤ 3.0% |
| 6 | LOD > 3.0% AND/OR LOR > 3.0% |

Table 3 presents six grades for categorizing the amount of porcelain, ceramics, stones, metals, and different glasses (such as borosilicate) that was determined to be in the measured sample. In the example of Table 3, grade 6 is a category 4—those piles of contaminated cullet that include a large number of large size objects, or a large weight percentage of small objects. With regards to the larger size objects, these can result in significant inclusions and weaknesses in a final glass product, and should therefore be minimized. With regards to contaminated cullet piles having a large weight percentage of such objects, it is appreciated that these are often miscellaneous contaminants sometimes referred to as dirt.

TABLE 3

Grading criteria and categories for PCS, metals and different glasses.

| Grade* | PCS, Metals and Different Glasses |
|---|---|
| 1 | Large size; 0-1 count AND/OR Small size ≤0.5 wt. % |
| 2 | Large size; 2 count AND/OR 0.5 < Small size ≤ 1.0 wt. % |
| 3 | Large size; 3 count AND/OR 1.0 < Small size ≤ 1.5 wt. % |
| 4 | Large size; 4 count AND/OR 1.5 < Small size ≤ 2.0 wt. % |
| 5 | Large size; 5 count AND/OR 2.0 < Small size ≤ 2.5 wt. % |
| 6 | Large size; 6 or more count AND/OR Small size >2.5 wt. % |

Table 4 shows six categories of grades that refer to cullet pieces that are either too small or too large. It has been determined that too many large pieces of cullet can impede the conveying systems that provide the cullet and other materials to the furnace. With regards to small pieces, it has been found that too many small pieces can result in high degrees of organic contamination.

TABLE 4

Grading criteria and categorizing for sizing of cullet pieces.

| Grade | Size of cullet pieces |
|---|---|
| 1 | off size ≤20% |
| 2 | 20% < off size ≤ 30% |
| 3 | 30% < off size ≤ 40% |
| 4 | 40% < off size ≤ 50% |
| 5 | 50% < off size ≤ 60% |
| 6 | off size >60% |

Figure 5:
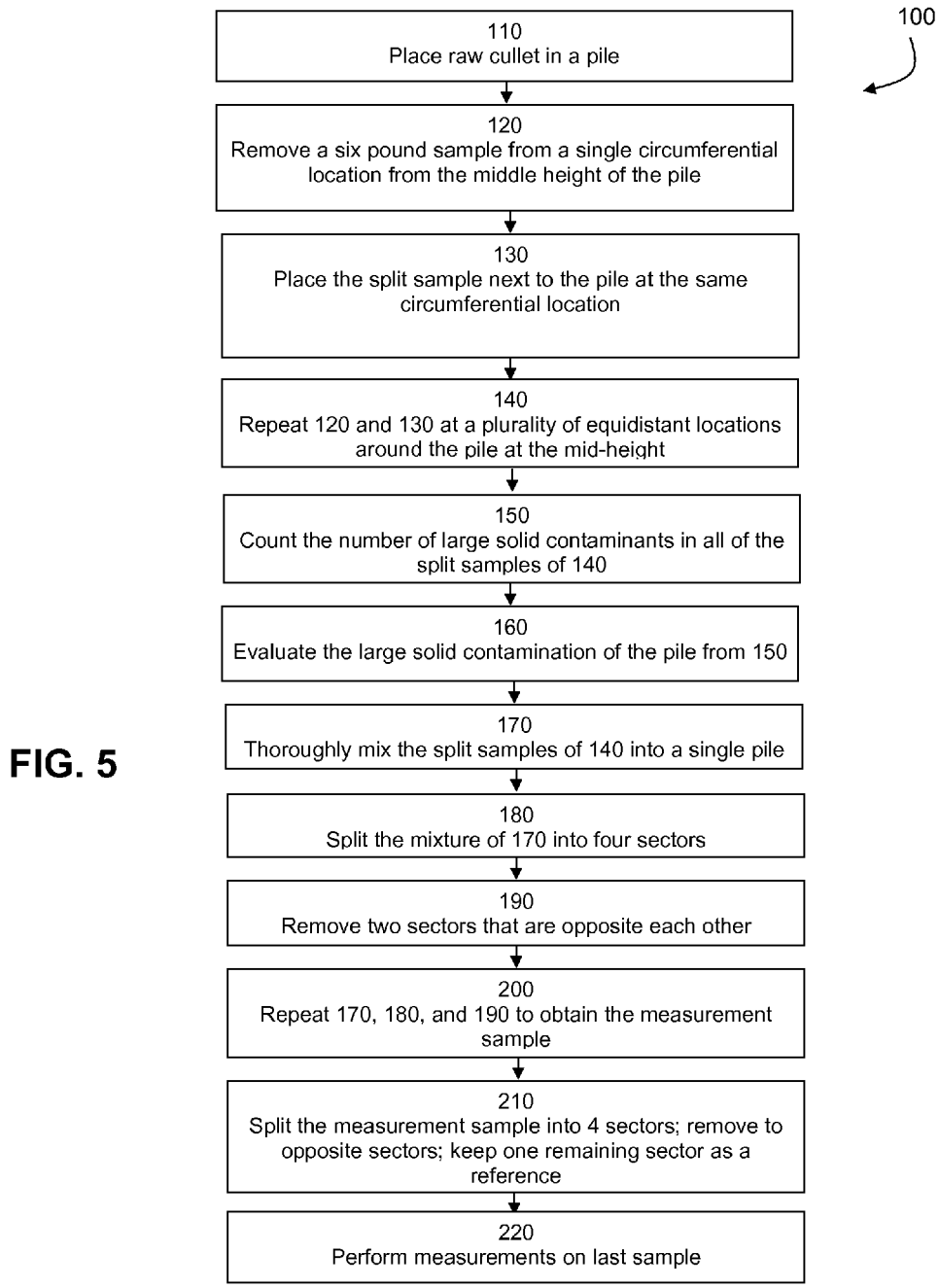
FIG. 5 is a block diagram of a method according to one embodiment of the present invention.
Figure 6:
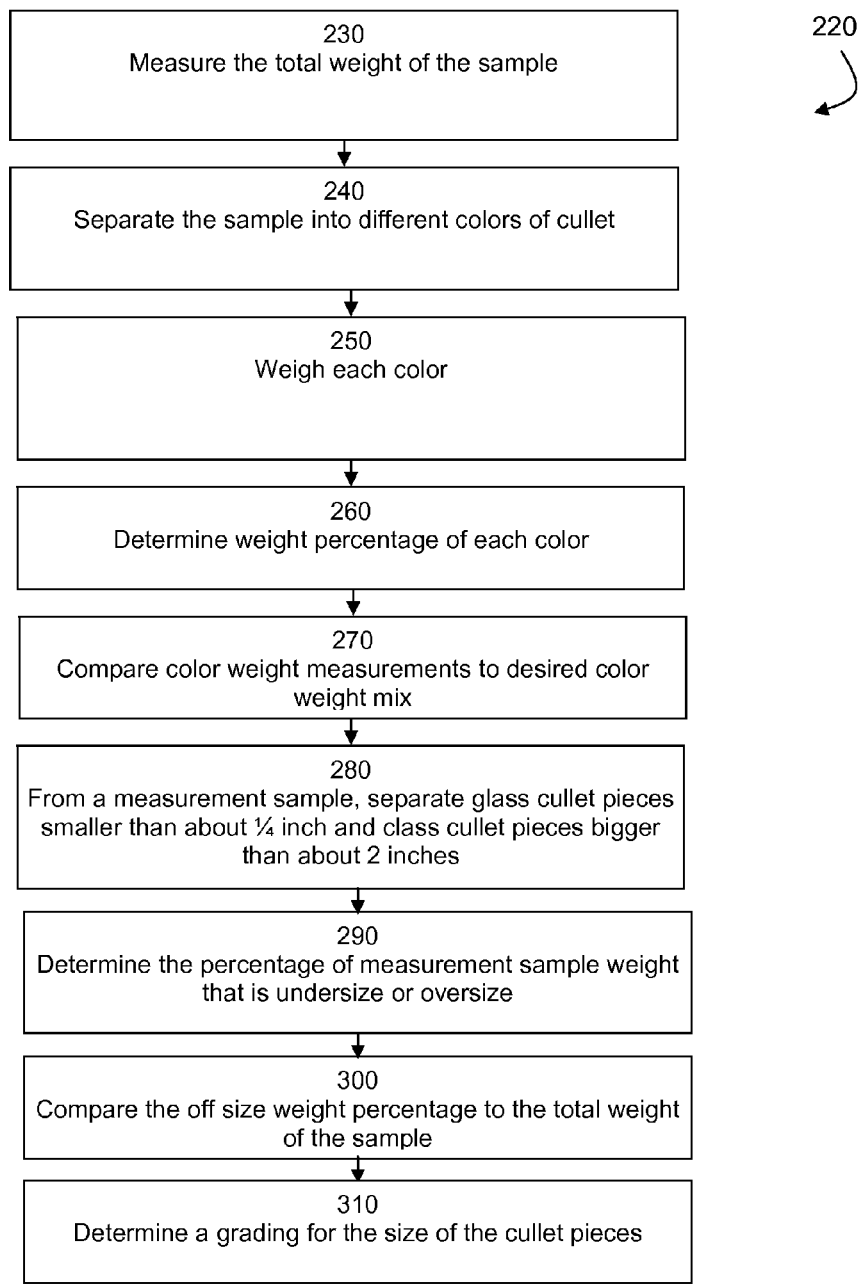
FIG. 6 is a block diagram of a method according to one embodiment of the present invention.
Figure 7:
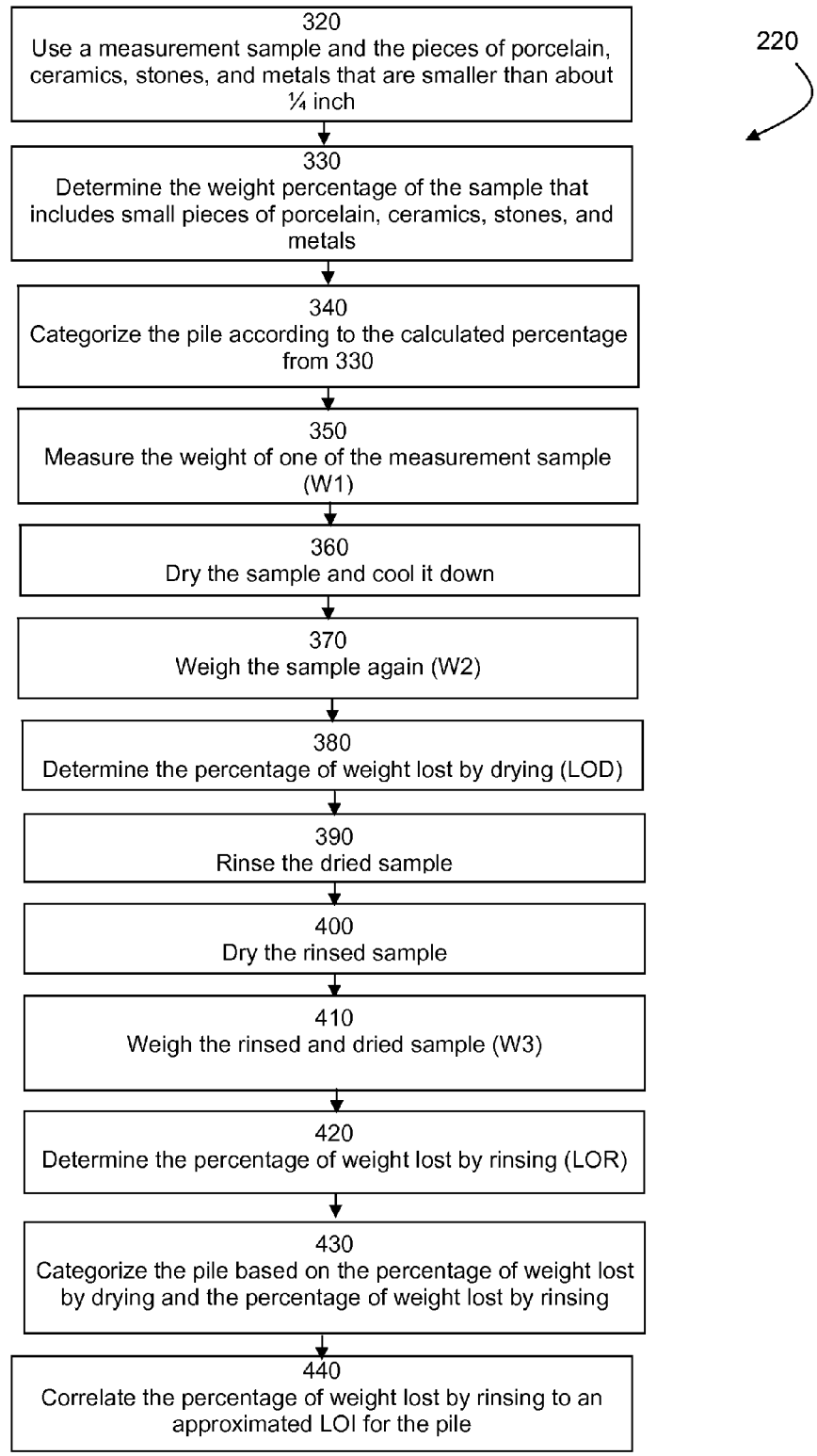
FIG. 7 is a block diagram of a method according to one embodiment of the present invention.

FIGS. 5, 6, and 7 show various embodiments of cullet evaluation method 100. Method 100 includes the act 110 of placing raw or contaminated cullet in a single pile. This may be all or part of a load of contaminated cullet within a truck, or piles created in other methods. Act 120 is to take a sample from predetermined circumferential location at a predetermined height of the pile. Act 130 includes taking the split sample from act 120 and placing it adjacent to the pile at about the same circumferential location. Act 140 includes repeating act 120 and 130 preferably at a plurality of equidistant circumferential locations, and preferably from about the same predetermined height of the pile. These additional split samples (as best seen in FIG. 3) can be thought of as being arranged along north, south, east, and west directions.

Act 150 includes counting the number of large solid contaminants in all of the individual split samples as shown in FIG. 3. This counting of large size particles is assessed within Table 3, as shown in act 160.

Following the evaluation of large solid contamination, act 170 includes mixing together the split samples (such as the eight split samples shown in FIG. 3) into a single mixture. The single mixture is then divided into four sectors, as expressed by act 180 and shown in FIG. 4. Two sectors that are opposite from one another are removed and placed back in the original pile (the sectors being indicated by cross hatched lines in FIG. 4). There are now two samples that are opposite each other in terms of an X-Y grid. In some embodiments, one of the sectors will include the measured sample that is used in act 220. In yet other embodiments, and as expressed in act 200, these two opposite sectors are again mixed, split, and separated in a repeat of acts 170, 180, and 190.

Further details of the measurement act 220 are shown in FIGS. 6 and 7. Acts 230 to 270 include an assessment of the weight percentage of different colors within the measured sample. The color weight measurements are compared to the desired color weight mix as expressed in Table 1.

Acts 280 to 310 pertain to the categorization and grading of cullet pieces in the measurement sample that are either too small or too large. As expressed in act 310, the percentage of cullet pieces smaller than a predetermined size or larger than a different predetermined size are graded according to the categories of Table 4.

FIG. 7 shows additional aspects of measurement method 220. Acts 320, 330, and 340 include separating the smaller pieces of porcelain, ceramics, stones, metals, and other glasses, determining their weight percentage as a total of the measurement sample, and categorizing the pile according to grades of table 3.

Steps 350 to 440 pertain to establishing values for the LOD and LOR qualities the pile. Act 350 includes measuring the weight of the measurement sample. Act 360 includes drying the sample, such as at 110 degrees C. and then cooling it down. The sample is again weighed, and in act 330 the percentage of weight lost by drying is established.

Figure 2:
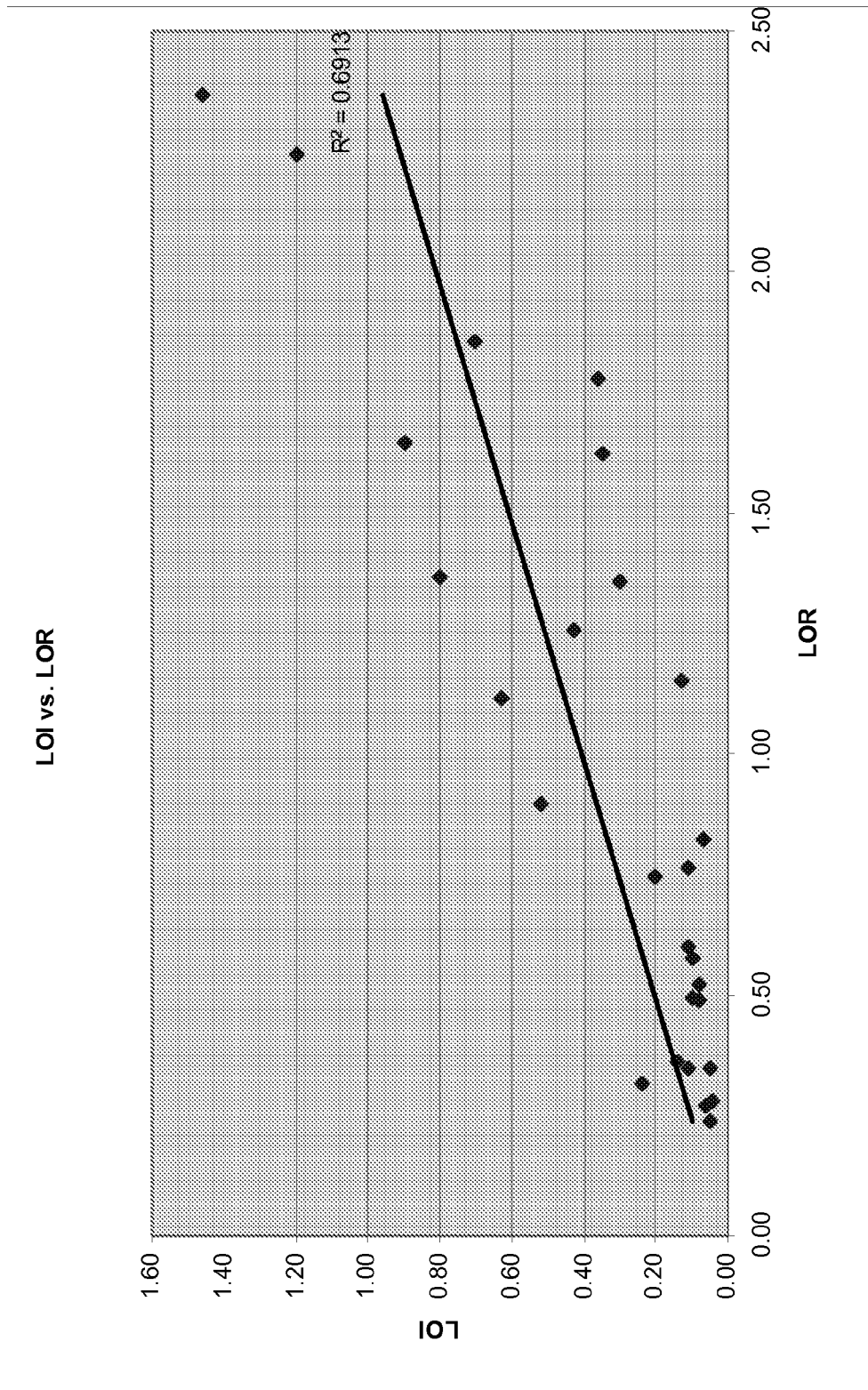
FIG. 2 is a graphical representation of the results of measured LOI at 500 degrees C. versus LOR on 27 different cullet samples, and is an approximate correlation to convert measured LOR to LOI.

In some embodiments, act 390 follows act 380, and includes rinsing the dried measurement sample. The rinsing is continued until the rinsing fluid is considered to be free of contaminants. In acts 400 and 410 the rinsed sample is dried and weighed, respectively. Act 420 includes determining the percentage of weight lost by the rinsing. Act 430 includes categorizing the pile based on the grading criteria of Table 2. Act 440 includes using the data of FIG. 2 to correlate LOR to LOI.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:
1. A method for evaluating cullet, comprising:
providing a quantity of cullet contaminated with other waste products;
removing a sample from the quantity of cullet;
counting the number of non-glass objects in the sample larger than a predetermined size;
associating a first numerical grade with the number;

separating from the sample one of amber cullet, green cullet, or flint cullet and determining a weight fraction of the separated cullet within the sample;

associating a second numerical grade with the weight fraction; and evaluating the quantity of the cullet for use in a glass furnace using the first numerical grade and the second numerical grade.

2. The method of claim 1 which further comprises drying the sample and determining a fraction of weight lost by drying and associating a third numerical grade with the fraction of weight lost by drying, wherein said evaluating uses the third numerical grade.

3. The method of claim 1 which further comprises rinsing the sample and determining a fraction of weight lost by rinsing and associating a third numerical grade with the fraction of weight lost by rinsing, wherein said evaluating uses the third numerical grade.

4. The method of claim 1 which further comprises rinsing the sample and determining a fraction of weight lost by rinsing and associating the fraction of weight lost by rinsing with the weight loss by ignition, wherein said evaluating uses the weight loss by ignition.

5. The method of claim 1 which further comprises determining a weight percentage of cullet particles smaller than a predetermined size in the sample and associating a third numerical grade with the weight percentage of cullet particles smaller than the predetermined size, wherein said evaluating uses the third numerical grade.

6. The method of claim 5 which further comprises determining a weight percentage of cullet particles larger than a second predetermined size in the sample and associating the third numerical grade with the weight percentage of cullet particles smaller than the predetermined size and the weight percentage of cullet particles larger than the second predetermined size large size, wherein said evaluating uses the third numerical grade.

\* \* \* \* \*